United States Patent
Kakony

(10) Patent No.: US 11,344,331 B2
(45) Date of Patent: May 31, 2022

(54) AUTOMATED HAIR RESTORATION ASSEMBLY

(71) Applicant: Rasim Kakony, Jackson, MI (US)

(72) Inventor: Rasim Kakony, Jackson, MI (US)

(*) Notice: Subject to any disclaimer, the term of this patent is extended or adjusted under 35 U.S.C. 154(b) by 212 days.

(21) Appl. No.: 16/855,412

(22) Filed: Apr. 22, 2020

(65) Prior Publication Data
US 2021/0330353 A1   Oct. 28, 2021

(51) Int. Cl.
*A61B 17/34* (2006.01)
*A61F 2/10* (2006.01)
*A61B 17/00* (2006.01)

(52) U.S. Cl.
CPC ........... *A61B 17/3468* (2013.01); *A61F 2/10* (2013.01); *A61B 2017/00752* (2013.01)

(58) Field of Classification Search
CPC ........ A61B 17/32002; A61B 17/32053; A61B 17/3468; A61B 2017/00752; A61F 2/10
See application file for complete search history.

(56) References Cited

U.S. PATENT DOCUMENTS

| | | | |
|---|---|---|---|
| 5,782,853 A | 7/1998 | Zeevi | |
| 6,221,088 B1 | 4/2001 | Bays | |
| 6,432,118 B1 | 8/2002 | Messerly | |
| D568,475 S | 5/2008 | Sandel | |
| 8,715,245 B2 | 5/2014 | Teufelberger | |
| 8,998,931 B2 | 4/2015 | Wesley | |
| 2003/0036770 A1* | 2/2003 | Markman | A61F 2/10 606/187 |

* cited by examiner

*Primary Examiner* — Ashley L Fishback

(57) ABSTRACT

An automated hair restoration assembly includes a control unit and a cylinder that is gripped during a hair restoration surgical procedure. An actuator is positioned within the cylinder and a turret unit is rotatably coupled to the cylinder. A plurality of cartridges is provided and a selected one of the cartridges is loadable into the turret unit. Each of the cartridges contains a respective one of a plurality of incising blades, a plurality of hair grafts or an alternating sequence of a plurality of said incising blades. The actuator passes through the respective tube and engages one of the incising blades or one of the hair grafts. Thus, each the incising blades can make a respective incision and each of the hair grafts is inserted into the respective incision.

10 Claims, 10 Drawing Sheets

AUTOMATED HAIR RESTORATION ASSEMBLY

CROSS-REFERENCE TO RELATED APPLICATIONS

Statement Regarding Federally Sponsored Research or Development

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to hair restoration devices and more particularly pertains to a new hair restoration device for automating the process of performing a hair restoration procedure.

BRIEF SUMMARY OF THE INVENTION

An embodiment of the disclosure meets the needs presented above by generally comprising a control unit and a cylinder that is gripped during a hair restoration surgical procedure. An actuator is positioned within the cylinder and a turret unit is rotatably coupled to the cylinder. A plurality of cartridges is provided and a selected one of the cartridges is loadable into the turret unit. Each of the cartridges contains a respective one of a plurality of incising blades, a plurality of hair grafts or an alternating sequence of a plurality of said incising blades. The actuator passes through the respective tube and engages one of the incising blades or one of the hair grafts. Thus, each the incising blades make a respective incision and each of the hair grafts is inserted into the respective incision.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
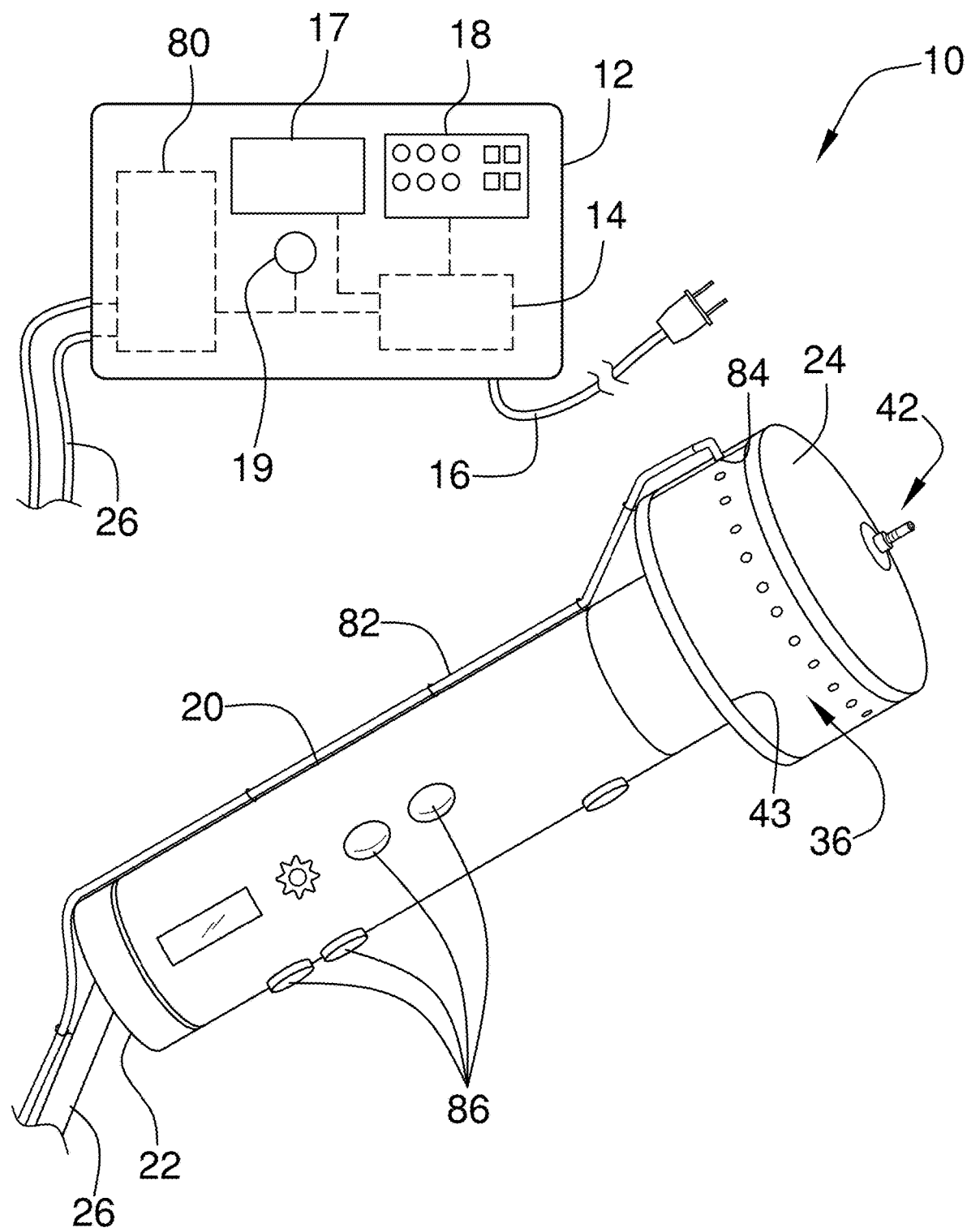
FIG. 1 is a perspective view of a cylinder and a turret unit of an automated hair restoration assembly according to an embodiment of the disclosure.
Figure 2:
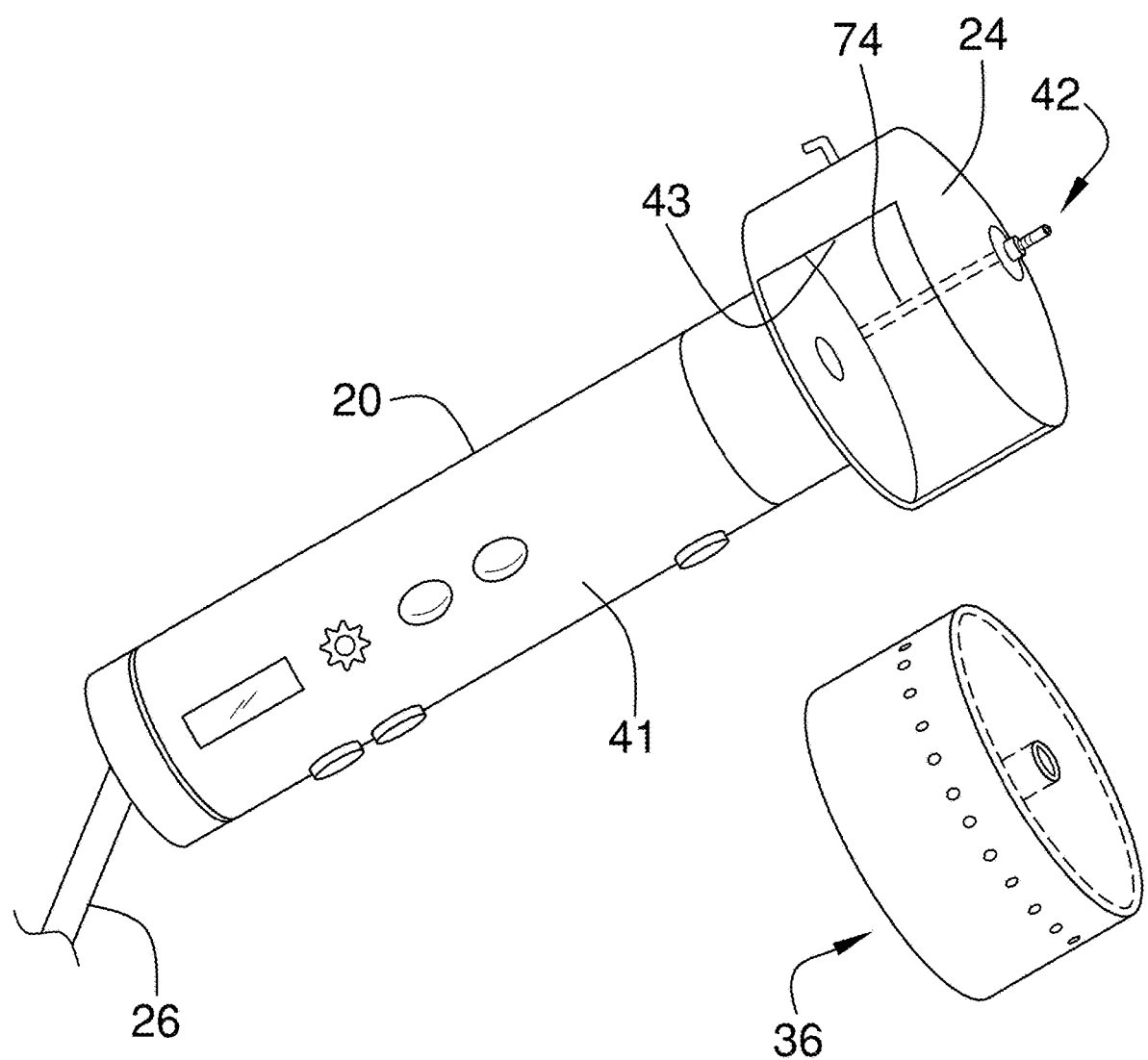
FIG. 2 is an exploded view of a cylinder and a turret unit of an embodiment of the disclosure.
Figure 3:
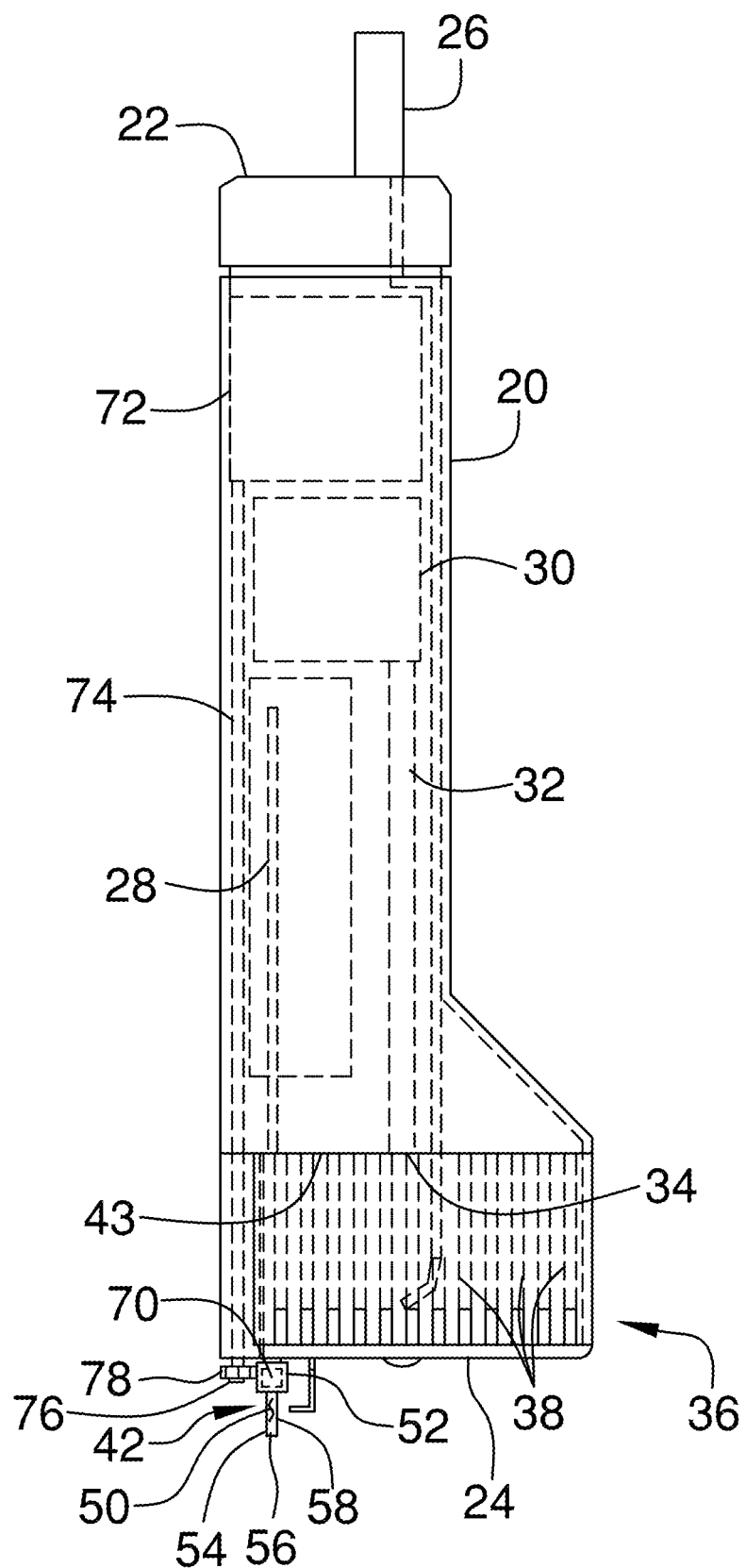
FIG. 3 is a phantom view of a cylinder and a turret unit of an embodiment of the disclosure.
Figure 4:
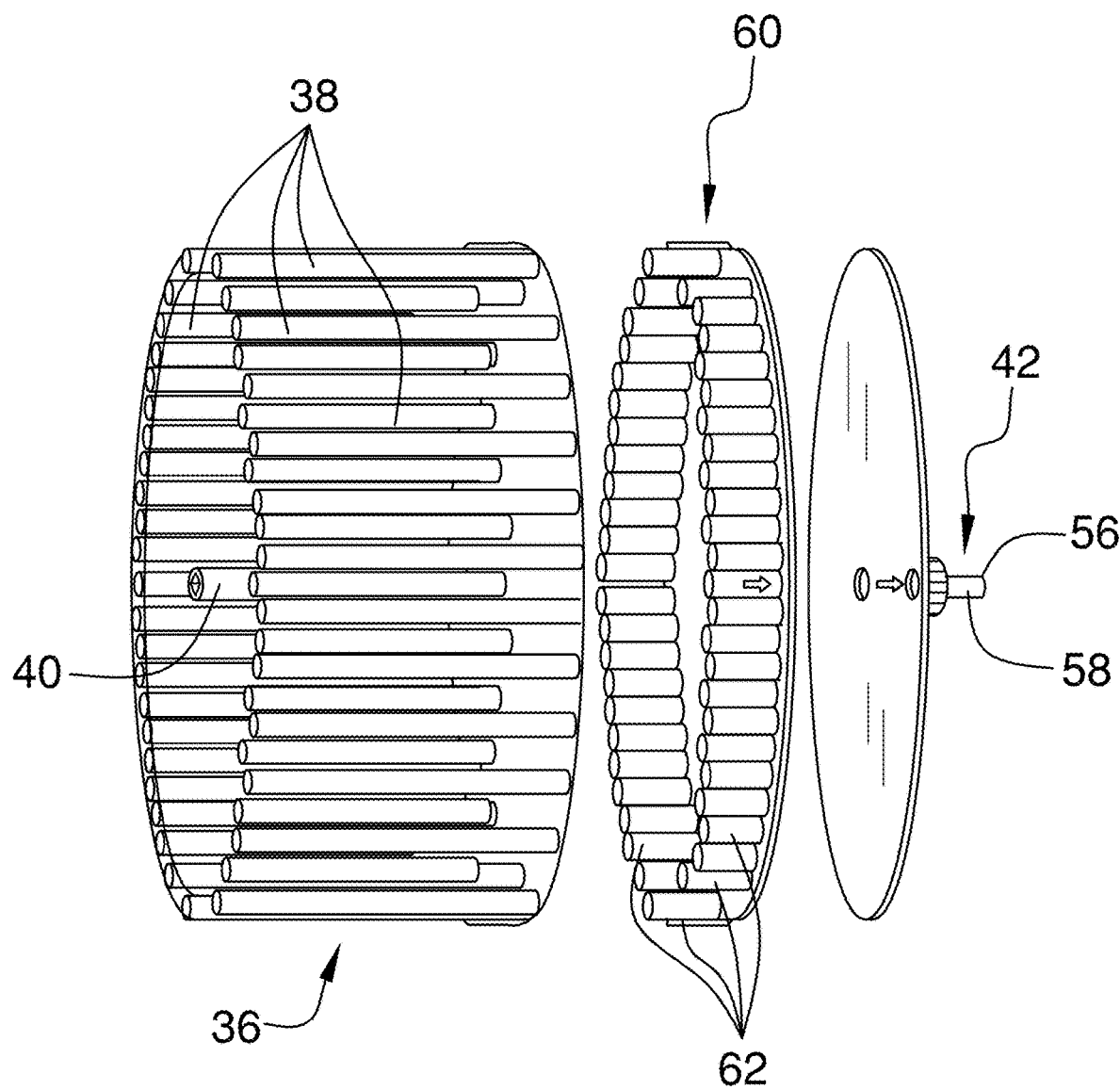
FIG. 4 is an exploded view of a turret unit and a graft cartridge of an embodiment of the disclosure.
Figure 5:
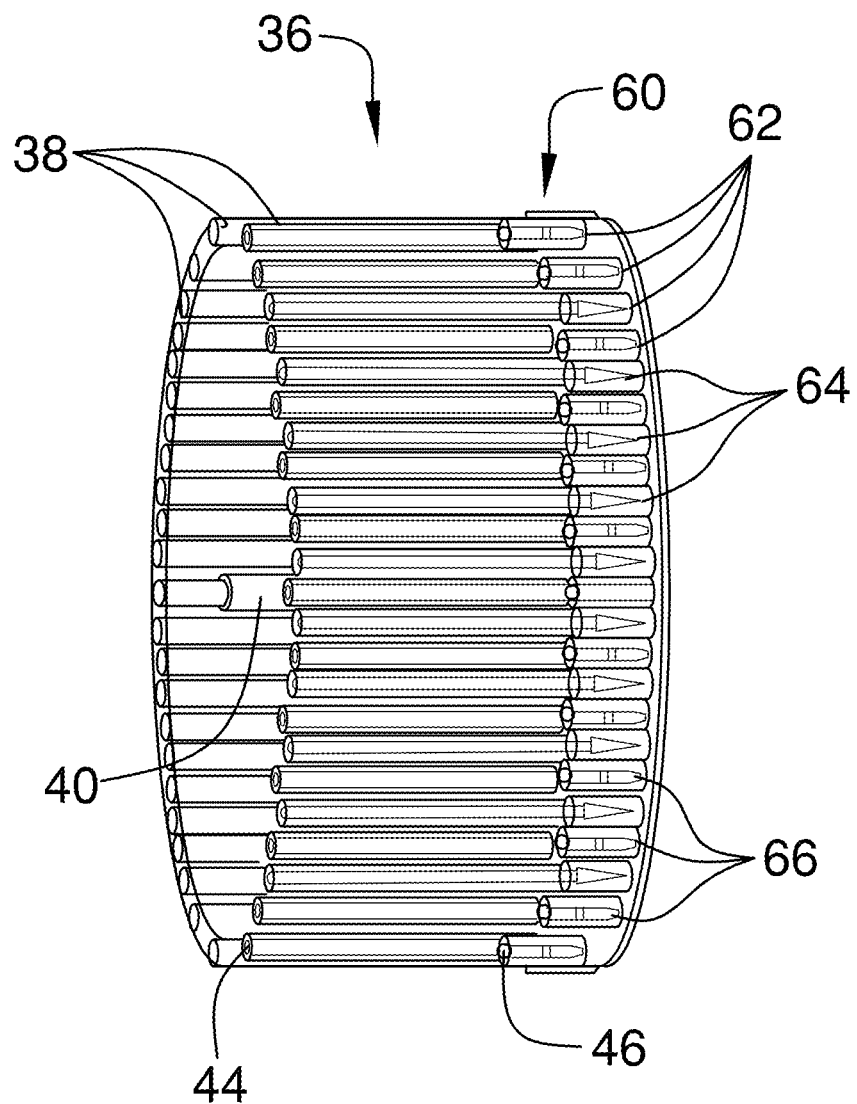
FIG. 5 is a top perspective view of a turret unit and an alternating cartridge of an embodiment of the disclosure.
Figure 6:
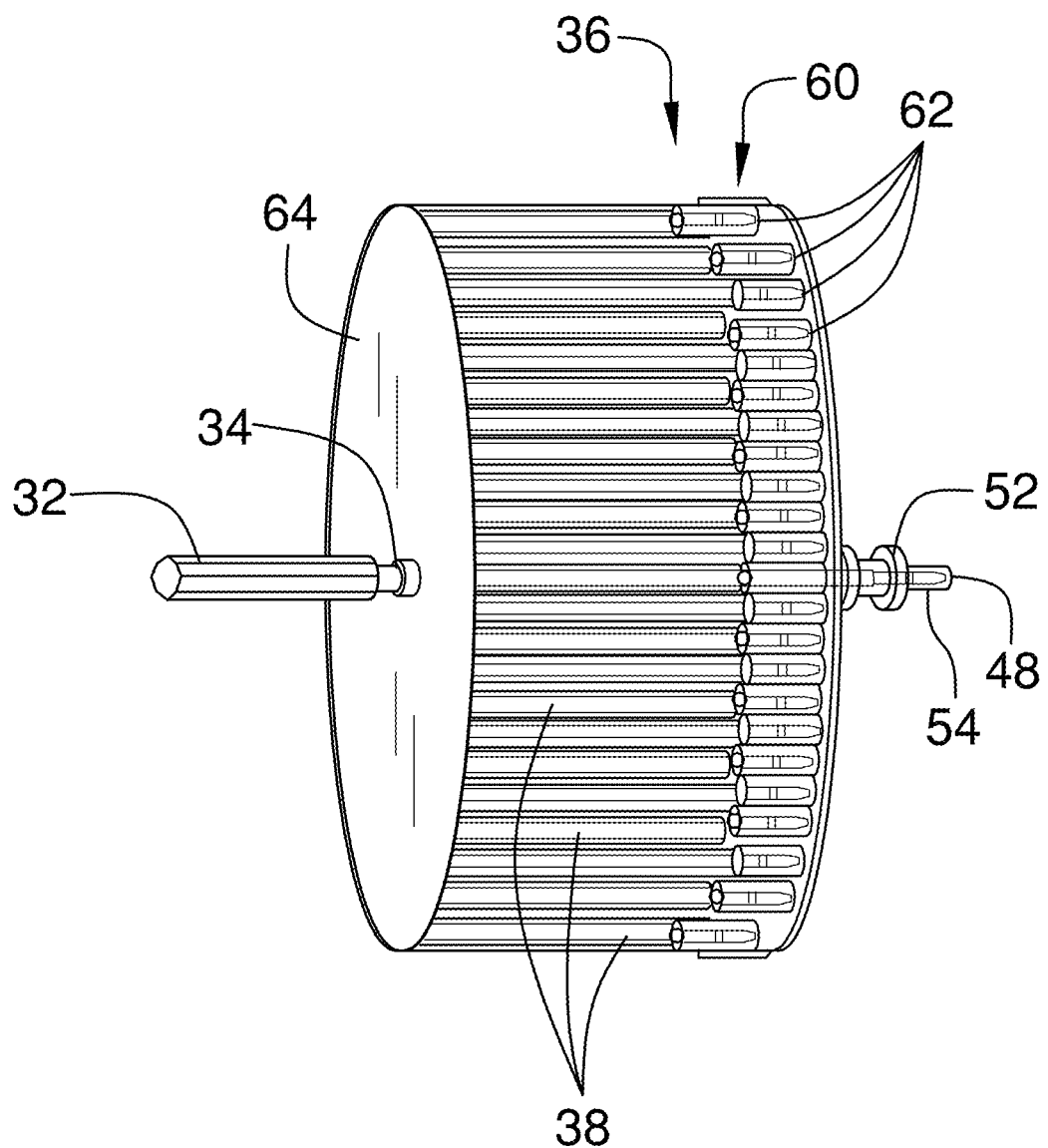
FIG. 6 is a front perspective view of a turret unit and graft cartridge of an embodiment of the disclosure.
Figure 7:
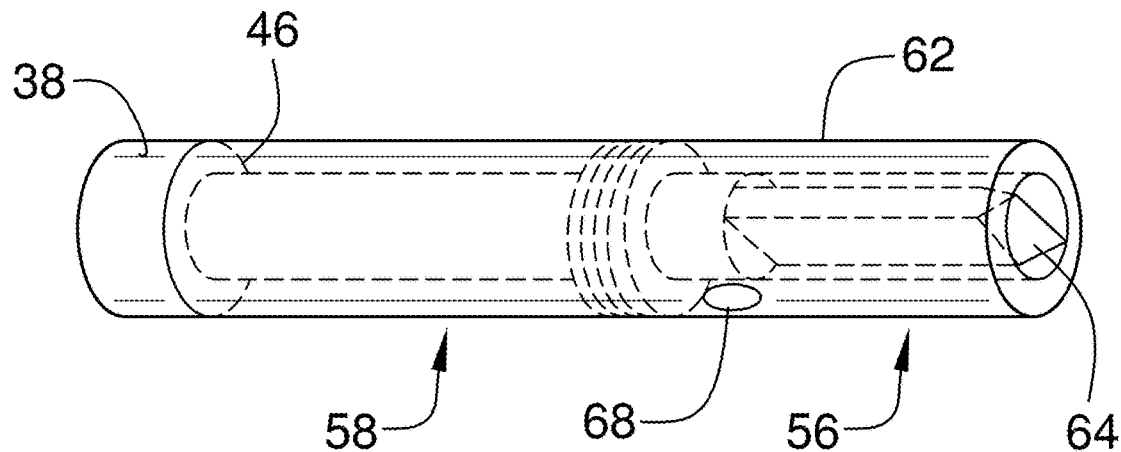
FIG. 7 is a phantom view of a sleeve containing an incising blade an embodiment of the disclosure.
Figure 8:
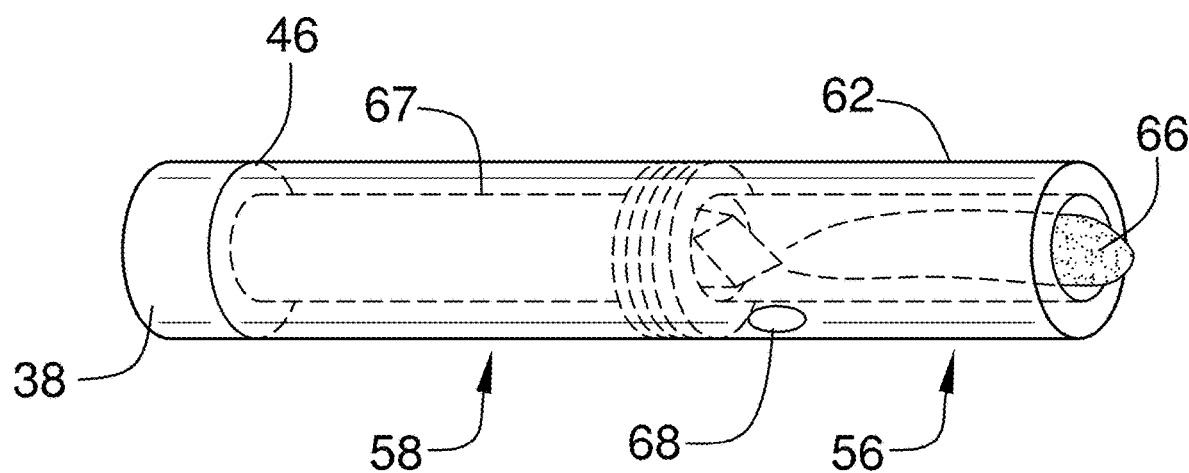
FIG. 8 is a phantom view of sleeve containing a hair graft of an embodiment of the disclosure.
Figure 9:
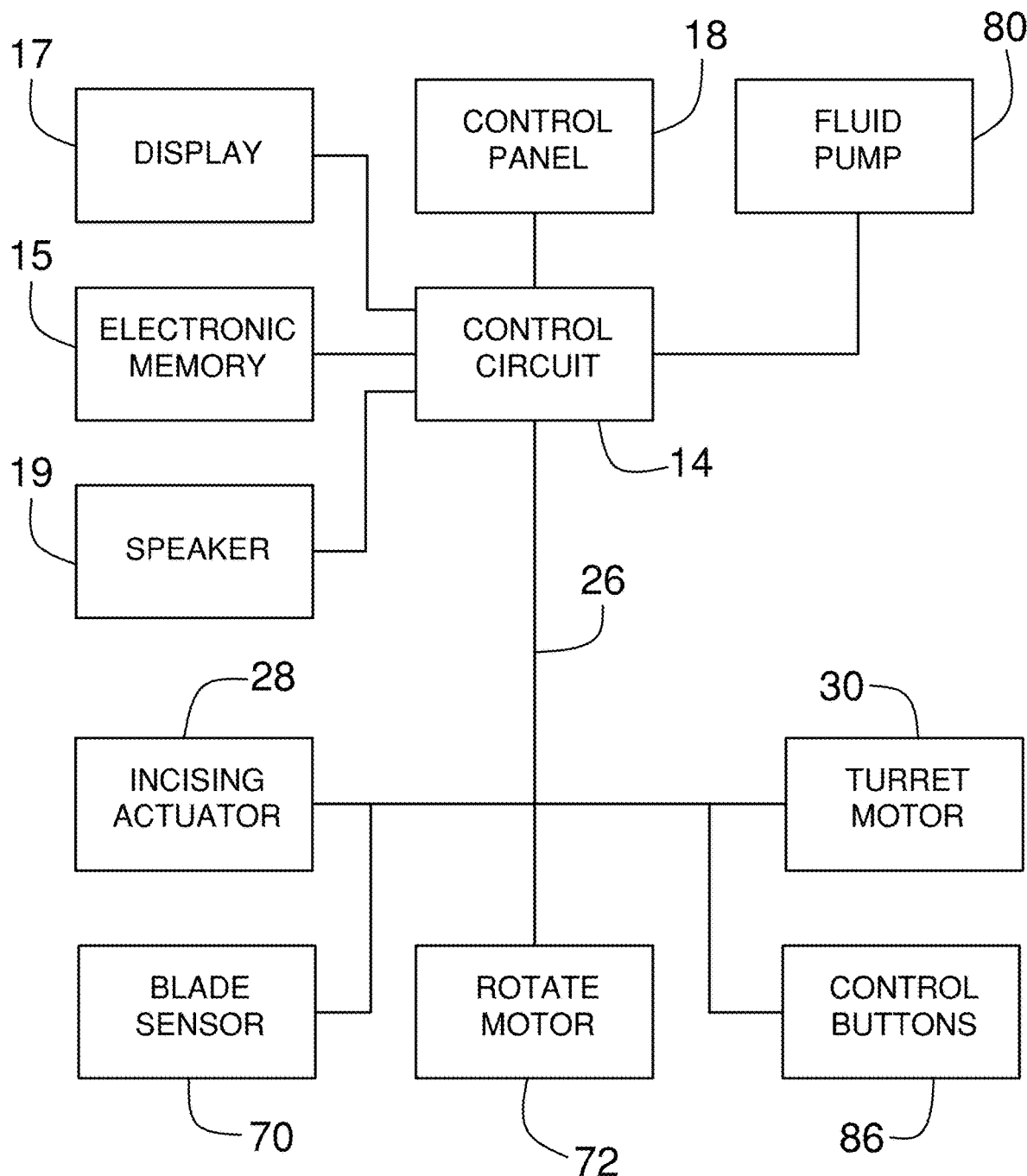
FIG. 9 is a schematic view of an embodiment of the disclosure.
Figure 10:
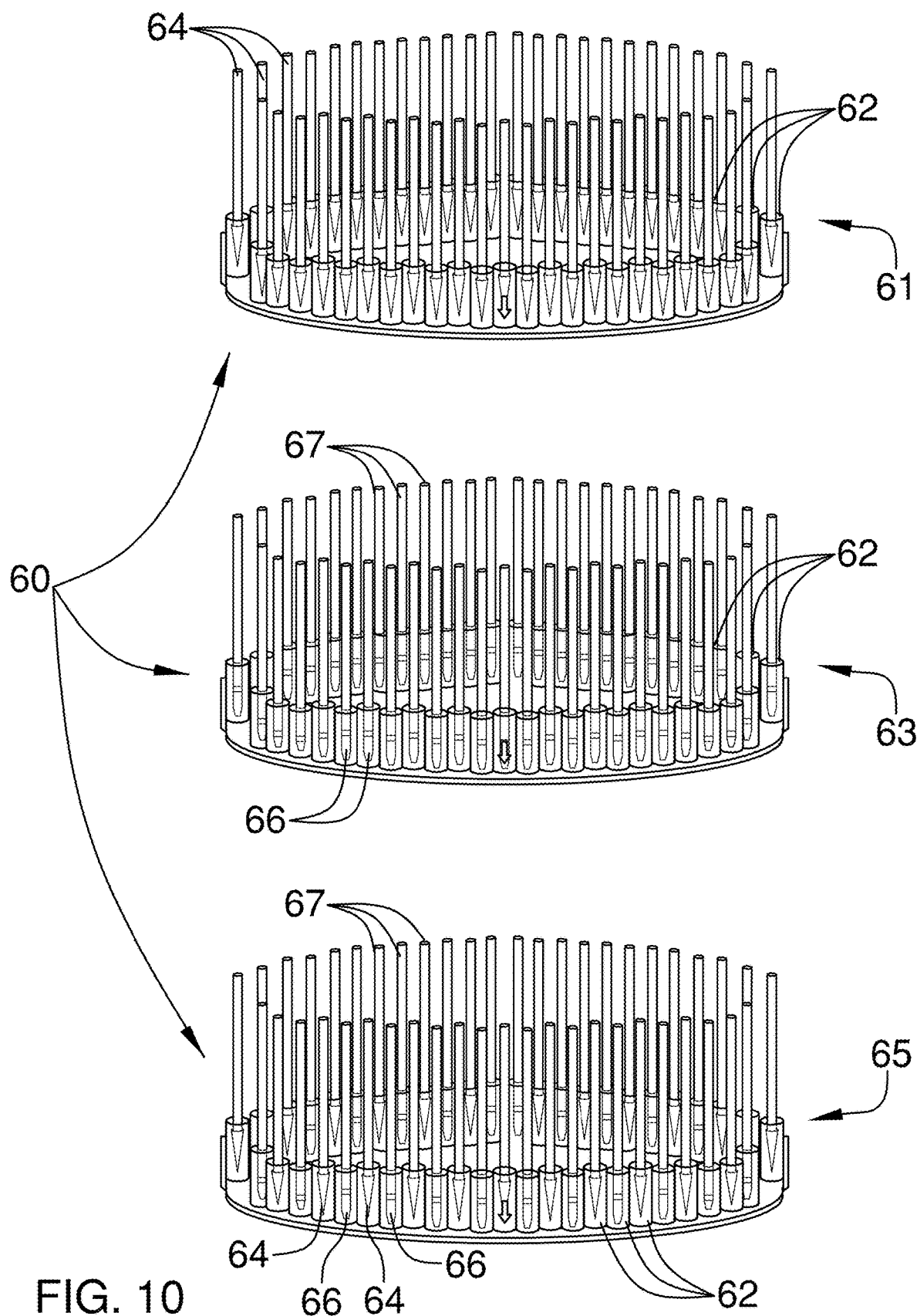
FIG. 10 is a perspective view of a plurality of cartridges of an embodiment of the disclosure.

With reference now to the drawings, and in particular to FIGS. 1 through 10 thereof, a new hair restoration device embodying the principles and concepts of an embodiment of the disclosure and generally designated by the reference numeral 11 will be described.

As best illustrated in FIGS. 1 through 10, the automated hair restoration assembly 10 generally comprises a control unit 12 that is positioned in a surgical room. The surgical room may be a room in which a hair restoration procedure is being performed. The control unit 12 includes a control circuit 14 and a power cord 16 that is electrically coupled to the control circuit 14. The power cord 16 is electrically coupled to a power source, such as a female electrical outlet or the like. Additionally, a control panel 18 is positioned on the control unit 12, the control panel 18 is electrically coupled to the control circuit 14 and the control panel 18 controls operational parameters of the control circuit 14. The control circuit 14 includes an electronic memory 15 that stores data pertaining to an incising configuration, a graft configuration and an implant configuration.

A display 17 is coupled to the control unit 12 and the display 17 is electrically coupled to the control circuit 14. The display 17 displays indicia comprising operational parameters, selected operational sequences, the number of incisions made or grafts inserted, and any other pertinent information for a user. The display 17 may comprise an LED or other type of electronic display. Additionally, a speaker 19 is coupled to the control unit 12 for emitting audible alerts to the user. The speaker 19 is electrically coupled to the control circuit 14 and the speaker 19 may emit audible reminders relating to the operation of the control unit 12.

A cylinder 20 is provided and the cylinder 20 gripped during a hair restoration surgical procedure. The cylinder 20 has a first end 22 and a second end 24, the cylinder 20 is hollow and the second end 24 is open. A conductor 26 is coupled between the first end 22 of the cylinder 20 and the control unit 12 and the conductor 26 is electrically coupled to the control circuit 14. An actuator 28 is positioned within the cylinder 20 and the actuator 28 is electrically coupled to the conductor 26. The actuator 28 is turned on to extend a pre-determined distance outwardly from the first end 22 of the cylinder 20. The actuator 28 may be a linear actuator, an extending actuator, and actuator arm or other similar mechanical actuator that travels a fixed distance between an extended position and a returned position. Additionally, the fixed distance may the optimum depth of a hair graft incision for obtaining the maximum effective depth for insertion of a hair graft while minimizing trauma to underlying blood vessels and tissue.

A turret motor 30 is positioned within the cylinder 20 and the turret motor 30 is electrically coupled to the conductor 26. The turret motor 30 rotates a pre-determined degree of rotation in a first direction when the turret motor 30 is turned on. The turret motor 30 may be an electric motor or the like and the control circuit 14 controls the degree of rotation. A turret shaft 32 is movably coupled to the turret motor 30, the turret shaft 32 has a distal end 34 with respect to the turret motor 30 and the distal end 34 is aligned with the second end 24 of the cylinder 20. The turret motor 30 urges the turret shaft 32 into an extended position or a retracted position.

A turret unit 36 is rotatably coupled to the cylinder 20 and the turret unit 36 has a plurality of tubes 38 that are distributed around a central shaft 40. The turret unit 36 has a dissector 42 that is rotatably located thereon, the dissector 42 is distally positioned with respect to the cylinder 20 and the dissector 42 is aligned with the actuator 28. The central shaft 40 engages the distal end 34 of the turret shaft 32 when the turret shaft 32 is urged into the extended position. In this way the turret unit 36 is retained in the cylinder 20. An outer wall 41 of the cylinder 20 may have a turret opening 43 extending into an interior of the cylinder 20 and the turret opening 43 may insertably receive the turret unit 36. The tubes 38 are oriented collinear with an axis extending through the first 22 and second 24 ends of the cylinder 20 when the turret unit 36 is coupled to the cylinder 20. Each of the tubes 38 is sequentially aligned between the dissector 42 and the actuator 28 when the turret unit 36 is rotated.

Each of the tubes 38 has a top end 44 and a bottom end 46, and the top end 44 of a respective one of the tubes 38 is aligned with the actuator 28 each time the turret motor 30 is turned on. The bottom end 46 of the respective tube 38 is aligned with the dissector 42 each time the turret motor 30 is turned on. The top end 44 of the respective tube 38 receives the actuator 28 when the actuator 28 is turned on. Moreover, the actuator 28 extends outwardly through the bottom end 46 of the respective tube 38 when the actuator 28 is turned on.

Figure 11:
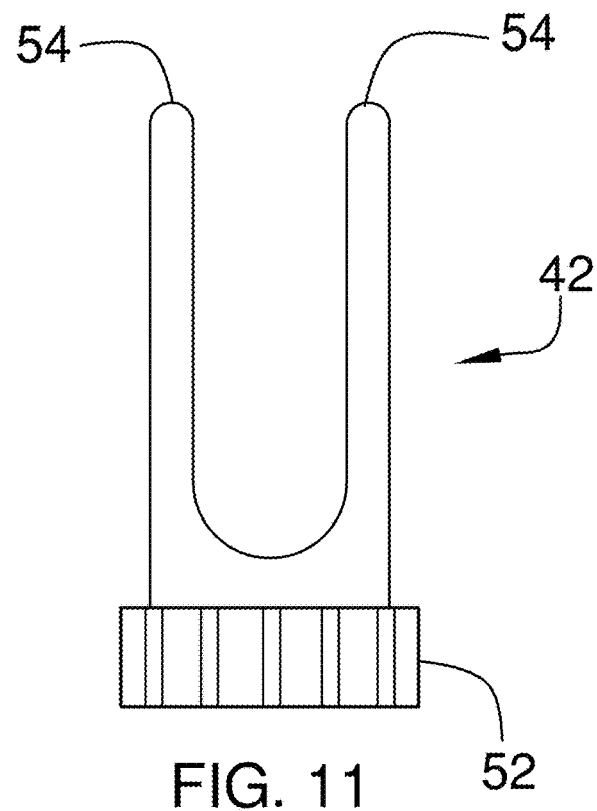
FIG. 11 is a perspective view of a dissector of an embodiment of the disclosure.
Figure 12:
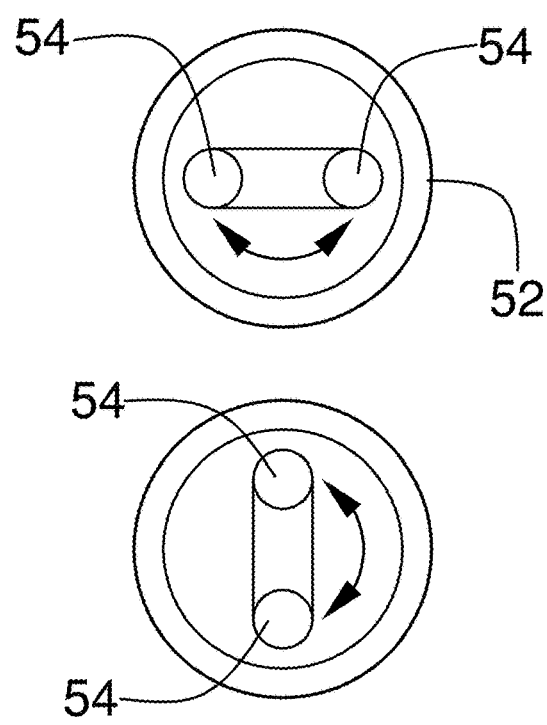
FIG. 12 is an end view showing a dissector being rotated between a spreading position and a home position.

The dissector 42 has a distal end 48 with respect to the turret unit 36 and an outer surface 50. The dissector 42 is rotatable about an axis extending through the turret unit 36 and the distal end 48 of the dissector 42. The distal end 48 of the dissector 42 is open, and dissector 42 includes a rounded portion 52 and a pair of fingers 54 each extending away from the rounded portion 52. The fingers 54 are spaced apart from each other a distance that is greater than the thickness of the fingers 54. The dissector 42 is rotatable between a home position and a spreading position. As is most clearly shown in FIG. 11, the fingers 54 are rotated 90.0 degrees when the dissector 42 is rotated between the home position and the spreading position. In this way the dissector 42 can be inserted into the incision when the dissector 42 is in the home position and the dissector 42 spreads the incision when the dissector 42 is in the spreading position.

A plurality of cartridges 60 is provided and selected one of the cartridges 60 is loadable into the turret unit 36. Each of the cartridges 60 has a plurality of sleeves 62 therein that are arranged into a circle. The plurality of sleeves 62 in each of the cartridges 62 may contain an alternating sequence of a plurality of incising blades 64 and a plurality of hair grafts 66. Each of the sleeves 62 has a fluid port 68 positioned thereon that is in fluid communication with an interior of the sleeves 62. Each of the incising blades 64 may be scalpel blades or the like that are common to hair restoration procedures. Each of the incising blades 64 is biased to be retracted into the respective sleeve. Additionally, each of the hair grafts 66 may be hair grafts commonly employed in hair restoration procedures. Each of the sleeves 62 is divided into a first section 56 that removably engages a second section 58.

The plurality of cartridges 60 includes an incising cartridge 61, a graft cartridge 63 and an alternating cartridge 65. As is most clearly shown in FIG. 7, the incising blades 64 extends through each of the first section 56 and the second section 58 of each of the sleeves 62 in the incising cartridge 61. The first section 56 of each of the sleeves 62 in the graft cartridge 63 is loaded with the hair grafts 66. Finally, each of the sleeves 62 in the alternating cartridge 65 is loaded with an alternating sequence of the incising blades 64 and the hair grafts 66. Each of the incising blades has a length that is greater than the length of the sleeves 62 and each of the hair grafts 66 includes a plunger 67. As is most clearly shown in FIG. 8, the plunger 67 extends through the second section 58 of the sleeves 62 and the hair grafts 66 extending through the first section 56 of the sleeves 62.

Each of the sleeves 62 is aligned and is oriented collinear with a respective one of the tubes 38 when the selected cartridge 60 is loaded into the turret unit 36. The actuator 28 passes through the respective tube 38 when the turret unit 36 is loaded into the turret opening 43 in the cylinder 20 and when the respective tube 38 is aligned with the actuator 28. Additionally, the actuator 28 engages one of the incising blades 64 or the plunger 67 on one of the hair grafts 66 thereby facilitating the incising blades 64 and the hair grafts 66 to be urged outwardly through the dissector 42. In this way each the incising blades 64 can make a respective incision and each of the hair grafts 66 can be inserted into the respective incision.

The incising cartridge 61 is loaded into the turret unit 36 for the first sequence, the graft cartridge 63 is loaded into the turret unit 36 for the second sequence and the alternating cartridge 65 is loaded into the turret unit 36 for the third sequence. The actuator 28 sequentially engages the incising blade 64 in each of the sleeves 62 when the incising cartridge is loaded into the turret unit 36. The actuator 28 sequentially engages the plunger 67 of the hair graft 66 in each of the sleeves 62 when the graft cartridge 63 is loaded into the turret unit 36. The actuator 28 engages, in an alternating sequence, the incising blade 64 and the plunger 67 of the hair graft 66 in each of the sleeves 62 when the alternating cartridge 65 is loaded into the turret unit 36.

The dissector 42 is urged into the respective incision when one of the incising blades 64 makes the respective incision having the dissector 42 being in the home position. Thus, the dissector 42 can subsequently guide the hair graft 66 into the respective incision. A blade sensor 70 is positioned within the dissector 42 and the blade sensor 70 is electrically coupled to the conductor 26. The control circuit 14 in the control unit 12 receives a blade input when the blade sensor 70 senses one of the incising blades 64 has been urged into the dissector 42. The blade sensor 70 may be a magnetic sensor or other electronic sensor that is capable of distinguishing between the incising blades 64 and the hair grafts 66.

A rotator motor 72 is positioned within the cylinder 20 and the rotator motor 72 is electrically coupled to the conductor 26. The rotator motor 72 rotates a pre-determined distance away from a home position and then a corresponding distance back toward the home position when the rotator motor 72 is turned on. Additionally, the rotator motor 72 is turned on when the control circuit 14 receives the blade input. The rotator motor 72 may be an electric motor or the like.

A rotator shaft 74 is rotatably coupled to the rotator motor 72 and the rotator shaft 74 has a distal end 76. A gear 78 is coupled to the distal end 76 of the rotator shaft 74 and the gear 78 engages the rounded portion 52 of the outer surface 50 of the dissector 42. The rotator motor 72 rotates the dissector 42 into the spreading position when the rotator motor 72 is turned on. Thus, the fingers 54 of the dissector 42 are rotated to spread the incision open to enhance the surgeon's ability to position the hair graft 66 within the respective incision. The rotator motor 72 rotates the dissector 42 back to the home position when the hair graft 66 has been inserted into the respective incision. The blade sensor 70 turns the rotator motor 72 on when the dissector 42 is pressed against the patient to rotate the dissector 42 into the spreading position. The blade sensor 70 turns the rotator motor 72 off when the dissector 42 is not pressed against the patient to rotate the dissector 42 into the home position. In this way the dissector 42 rotates into the spreading position and then into the home position each time the dissector 42 is pressed against the patient.

A fluid pump 80 is positioned in the control unit 12 and the fluid pump 80 contains a liquid solution. The liquid solution may be saline or other liquid solution that would commonly be employed in the hair restoration procedure. The fluid pump 80 includes a fluid hose 82 that extends between the control unit 12 and the turret unit 36. The fluid hose 82 has a distal end 84 with respect to the control unit 12. The fluid port 68 on each of the sleeves 62 is aligned with the distal end 84 of the fluid hose 82 each time the turret unit 36 is rotated thereby facilitating the fluid pump 80 to urge the liquid solution into the incision for nourishing the hair graft 66 in the incision.

A plurality of control buttons 86 is each of the control buttons 86 is movably coupled to the cylinder 20 and each of the control buttons 86 is electrically coupled to the conductor 26. Each of the control buttons 86 is assigned to control operational parameters of a respective one of the actuator 28, the turret motor 30, the rotator motor 72 and the fluid pump 80. The control circuit 14 contains data for a first sequence, a second sequence and a third sequence. The first sequence involves the turret unit 36 being rotated one place each time the turret motor 30 is turned on thereby lining up the incising blades 64 in the incising cartridge 61 with the actuator 28. Thus, the actuator 28 makes repeated incisions during the hair restoration procedure.

The second sequence involves the turret unit 36 being rotated one place each time the turret motor 30 is turned on. Additionally, the actuator 28 engages the plunger 67 of each of the hair grafts 66 when the graft cartridge 63. In this way the actuator 28 inserts one of the hair grafts 66 into pre-made incisions. The dissector is rotated between the home position and the spreading position each time the actuator 28 engages the plunger 67. The third sequence involves the turret unit 36 being rotated one place each time the turret motor 30 is turned on. Moreover, the fluid pump 80 is turned on each time the incision actuator 28 engages one of the hair grafts 66. In this way the hair graft 66 is moisturized or otherwise nourished when the hair graft 66 is inserted into the incision. Additionally, the rotator motor 72 is turned on each time the actuator 28 engages one of the incising blades 64. Thus, the incision is spread open to ensure adequate penetration of the hair graft 66 into the incision.

In use, the control panel 18 on the control unit 12 is manipulated to select the first sequence, the second sequence or the third sequence. Additionally, either the incising cartridge 61, the graft cartridge 63 or the alternating cartridge 65 is loaded into the turret unit 36. The cylinder 20 is gripped and the dissector 42 is positioned against the scalp for the hair restoration procedure. The turret unit 36 rotates one place each time the actuator 28 engages one of the incising blades 64 when the first sequence is selected. Thus, the process of making a plurality of incisions for a hair restoration procedure is automated.

The turret unit 36 rotates one place each time the actuator 28 engages the plunger 67 of the hair grafts 66 in the cartridges 60 when the second sequence is selected. In this way the process of inserting a hair graft 66 into the incision is automated. Additionally, the fluid pump 80 can introduce the fluid into the incision once the hair graft 66 has been inserted into the incision when the third sequence is selected. In this way an individual surgeon can perform multiple steps in a hair restoration surgery with a single tool. The turret unit 36 rotates one place each time the actuator engages the alternating sequence of incising blades 64 and hair grafts 66 when the third sequence is selected. In this way the process of making an incision and inserting a hair graft 66 into the incision is automated.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An automated hair restoration assembly being configured to make a hair graft incision and insert a hair graft into the hair graft incision, said assembly comprising:
   a control unit configured to be positioned in a surgical room, said control unit including a control circuit and a power cord being electrically coupled to said control circuit, said power cord being electrically coupled to a power source;
   a cylinder being gripped during a hair restoration surgical procedure;
   an actuator being positioned within said cylinder;
   a turret unit being rotatably coupled to said cylinder, said turret unit having a plurality of tubes being distributed around a central shaft, said turret unit engaging a dissector being rotatably located on said cylinder, each of said tubes being sequentially aligned between said dissector and said actuator when said turret unit is rotated;
   a plurality of cartridges, a selected one of said cartridges being loadable into said turret unit, each of said cartridges having a plurality of sleeves therein being arranged into a circle, said plurality of sleeves on each of said cartridges containing a respective one of a plurality of incising blades, a plurality of hair grafts or an alternating sequence of a plurality of said incising blades and a plurality of said hair grafts, each of said sleeves being aligned and being oriented collinear with a respective one of said tubes when said selected cartridge is loaded into said turret unit, an incising cartridge passing through said respective tube when said respective tube is aligned with said incising cartridge and engaging one of said incising blades or one of said hair grafts thereby facilitating said incising blades and said hair grafts to be sequentially urged outwardly through said dissector wherein each said incising blades are configured to make a respective incision and each of said hair grafts are configured to be inserted into the respective incision; and
   a plurality of control buttons, each of said control buttons being movably coupled to said cylinder, each of said control buttons being electrically coupled to a conductor, each of said control buttons being assigned to control operational parameters of a respective one of said actuator, said turret motor, said rotator motor and said fluid pump.

2. The assembly according to claim 1, wherein:
   said cylinder has a first end and a second end, said cylinder being hollow, said second end being open;
   said conductor being coupled between said first end of said cylinder and said control unit, said conductor being electrically coupled to said control circuit; and
   said actuator is electrically coupled to said conductor, said actuator being turned on to extend a pre-determined distance outwardly from said first end of said cylinder.

3. The assembly according to claim 2, further comprising:
   a turret motor being positioned within said cylinder, said turret motor rotating a pre-determined degree of rotation in a first direction when said turret motor is turned on; and
   a turret shaft being rotatably coupled to said turret motor, said turret shaft having a distal end with respect to said turret motor, said distal end being aligned with said second end of said cylinder.

4. The assembly according to claim 2, wherein:
   said dissector is positioned on said second end of said cylinder, said dissector being aligned with said actuator;
   said central shaft is coupled to said distal end of said turret shaft having said tubes being oriented collinear with an axis extending through said first and second ends of said cylinder, each of said tubes having a top end and a bottom end, said top end of a respective one of said tubes being aligned with said actuator each time said turret motor is turned on, said bottom end of said respective tube being aligned with said dissector each time said turret motor is turned on;
   said top end of said respective tube receives said actuator when said actuator is turned on having said actuator extending outwardly through said bottom end of said respective tube.

5. The assembly according to claim 4, wherein:
   said dissector has a distal end with respect to said second end of said cylinder and an outer surface, said dissector being rotatable about an axis extending through said first end and said second end of said cylinder, said distal end of said dissector being open; and
   said dissector having a rounded portion and a pair of fingers extending away from said rounded portion, said fingers being spaced apart from each other, said dissector being rotatable between a home position and a spreading position.

6. The assembly according to claim 5, wherein said dissector is urged into the respective incision when one of said incising blades makes the respective incision having said dissector being in said home position wherein said dissector is positioned to subsequently guide the hair graft into the respective incision, said wide side of said rectangular portion of said dissector being oriented to extend longitudinally along the respective incision when said dissector is in said home position.

7. The assembly according to claim 6, further comprising a rotator motor being positioned within said cylinder, said rotator motor being electrically coupled to said conductor, said rotator motor rotating a pre-determined distance away from a home position and then a corresponding distance back toward said home position when said rotator motor is turned on, said rotator motor being turned on when said control circuit receives said blade input.

8. The assembly according to claim 7, further comprising:
   a rotator shaft being rotatably coupled to said rotator motor, said rotator shaft having a distal end; and
   a gear being coupled to said distal end of said shaft, said gear engaging said rounded portion of said outer surface of said dissector, said rotator motor rotating said dissector into said spreading position when said rotator motor is turned on thereby facilitating said wide side of said rectangular portion of said dissector to be oriented to extend laterally across the respective incision wherein said dissector is configured to spread the incision for enhancing position the hair graft within the respective incision, said rotator motor rotating said dissector back to said home position when the hair graft has been inserted into the respective incision.

9. The assembly according to claim 1, further comprising a fluid pump being positioned in said control unit, said fluid pump containing a liquid solution, said fluid pump including a fluid hose extending between said control unit and said turret unit, said fluid hose having a distal end with respect to said control unit, each of said sleeves having a fluid port being positioned thereon and being in fluid communication with an interior of said sleeves, said fluid port on each of said sleeves being aligned with said distal end of said fluid hose each time said turret unit is rotated thereby facilitating said fluid pump to urge the liquid solution into the incision for nourishing the hair graft.

10. An automated hair restoration assembly being configured to make a hair graft incision and insert a hair graft into the hair graft incision, said assembly comprising:
- a control unit configured to be positioned in a surgical room, said control unit including a control circuit and a power cord being electrically coupled to said control circuit, said power cord being electrically coupled to a power source;
- a cylinder being gripped during a hair restoration surgical procedure, said cylinder having a first end and a second end, said cylinder being hollow, said second end being open;
- a conductor being coupled between said first end of said cylinder and said control unit, said conductor being electrically coupled to said control circuit;
- an actuator being positioned within said cylinder, said actuator being electrically coupled to said conductor, said actuator being turned on to extend a pre-determined distance outwardly from said first end of said cylinder;
- a turret motor being positioned within said cylinder, said turret motor being electrically coupled to said conductor, said turret motor rotating a pre-determined degree of rotation in a first direction when said turret motor is turned on;
- a turret shaft being rotatably coupled to said turret motor, said turret shaft having a distal end with respect to said turret motor, said distal end being aligned with said second end of said cylinder;
- a turret unit being rotatably coupled to said cylinder, said turret unit having a plurality of tubes being distributed around a central shaft, said turret unit engaging a dissector being rotatably located on said second end of said cylinder, said dissector being aligned with said actuator, said central shaft being coupled to said distal end of said turret shaft having said tubes being oriented collinear with an axis extending through said first and second ends of said cylinder, each of said tubes being sequentially aligned between said dissector and said actuator when said turret unit is rotated, each of said tubes having a top end and a bottom end, said top end of a respective one of said tubes being aligned with said actuator each time said turret motor is turned on, said bottom end of said respective tube being aligned with said dissector each time said turret motor is turned on, said top end of said respective tube receiving said actuator when said actuator is turned on having said actuator extending outwardly through said bottom end of said respective tube, said dissector having a distal end with respect to said turret and an outer surface, said dissector being rotatable about an axis extending through said turret unit and said distal end of said dissector, said distal end of said dissector being open, said dissector having a rounded portion and a pair of fingers extending away from said rounded portion, said fingers being spaced apart from each other, said dissector being rotatable between a home position and a spreading position;
- a plurality of cartridges, a selected one of said cartridges being loadable into said turret unit, each of said cartridges having a plurality of sleeves therein being arranged into a circle, said plurality of sleeves on each of said cartridges containing a respective one of a plurality of incising blades, a plurality of hair grafts of an alternating sequence of a plurality of said incising blades and a plurality of said hair grails, each of said sleeves being aligned and being oriented collinear with a respective one of said tubes when said selected cartridge is loaded into said turret unit, an incising cartridge passing through said respective tube when said respective tube is aligned with said incising cartridge and engaging one of said incising blades or one of said hair grafts thereby facilitating said incising blades and said hair grafts to be sequentially urged outwardly through said dissector wherein each said incising blades are configured to make a respective incision and each of said hair grafts are configured to be inserted into the respective incision, said dissector being urged into the respective incision when one of said incising blades makes the respective incision having said dissector being in said home position wherein said dissector is positioned to subsequently guide the hair graft into the respective incision, said wide side of said rectangular portion of said dissector being oriented to extend longitudinally along the respective incision when said dissector is in said home position, each of said sleeves having a fluid port being positioned thereon and being in fluid communication with an interior of said sleeves;
- a blade sensor being positioned within said dissector, said blade sensor being electrically coupled to said conductor, said control circuit in said control unit receiving a blade input when said blade sensor senses one of said incising blades has been urged into said dissector;
- a rotator motor being positioned within said cylinder, said rotator motor being electrically coupled to said conductor, said rotator motor rotating a pre-determined distance away from a home position and then a corresponding distance back toward said home position when said rotator motor is turned on, said rotator motor being turned on when said control circuit receives said blade input;
- a rotator shaft being rotatably coupled to said rotator motor, said rotator shaft having a distal end;
- a gear being coupled to said distal end of said rotator shaft, said gear engaging said rounded portion of said outer surface of said dissector, said rotator motor rotating said dissector into said spreading position when said rotator motor is turned on wherein said dissector is configured to spread the incision for enhancing position the hair graft within the respective incision, said rotator motor rotating said dissector back to said home position when the hair graft has been inserted into the respective incision;
- a fluid pump being positioned in said control unit, said fluid pump containing a liquid solution, said fluid pump including a fluid hose extending between said control unit and said turret unit, said fluid hose having a distal end with respect to said control unit, said fluid port on each of said sleeves being aligned with said distal end of said fluid hose each time said turret unit is rotated thereby facilitating said fluid pump to urge the liquid solution into the incision for nourishing the hair graft; and
- a plurality of control buttons, each of said control buttons being movably coupled to said cylinder, each of said control buttons being electrically coupled to said conductor, each of said control buttons being assigned to control operational parameters of a respective one of said actuator, said turret motor, said rotator motor and said fluid pump.

\* \* \* \* \*